April 19, 1955 H. C. SWIM Plant Pat. 1,382
ROSE PLANT
Filed March 3, 1954
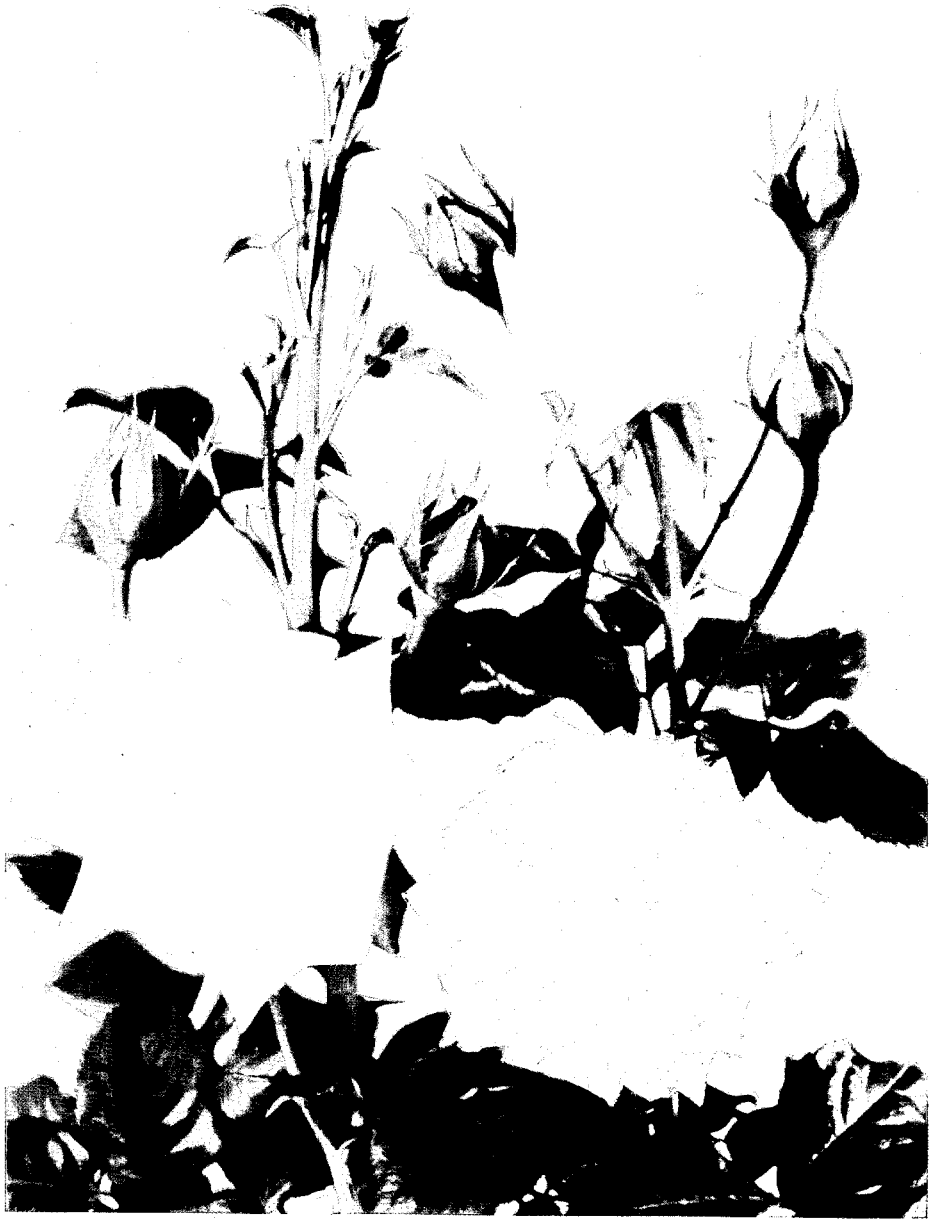
Inventor.
H. C. Swim
By: Robert Robb
Attorneys.

United States Patent Office

Plant Pat. 1,382

Patented Apr. 19, 1955

1,382

ROSE PLANT

Herbert C. Swim, Ontario, Calif., assignor to Armstrong Nurseries, Inc., Ontario, Calif., a corporation of California Application March 3, 1954, Serial No. 413,982

1 Claim. (Cl. 47—61)

The present invention relates to a new and distinct variety of rose plant of the hybrid polyantha class, which was originated by me by crossing the variety "Fandango" (Plant Patent No. 894) with the variety "Pinocchio" (Plant Patent No. 484).

The primary objective in making this cross was to produce a new variety of rose plant which combines the most desirable characteristics of the two parent varieties. This objective was fully achieved, as evidenced by the fact that my new variety is characterized by an unusual and distinctive color progression of its blooms which at first are yellow, with some markings of pink and salmon, but which change later to almost entirely pink and salmon in the older blooms. In addition to this unique color progression characteristic, my new variety is characterized by its abundant and semi-glossy foliage, as inherited from the parent "Fandango," by a petal substance comparable to that of the variety "Pinocchio," with attendant long-lasting quality of its blooms, by the moderate fragrance of its blooms as inherited from both parent varieties, and by the many-flowered cluster habit of its blooms as inherited from the variety "Pinocchio."

In comparison with its seed parent, "Fandango," my new variety is definitely distinguished from this parent by virtue of the fact that the blooms of the new variety are multicolored, whereas those of "Fandango" are bright red in color; the blooms of the new variety are very double in their petalage, having from 45 to 58 petals, whereas those of "Fandango" are semi-double and have only from 16 to 25 petals; the blooms of my new variety are borne in many-flowered clusters, whereas those of "Fandango" are usually borne singly, although sometimes 2 or 3 to a stem; and the petal substance of the blooms of my new variety is substantially greater than that of "Fandango."

As compared with its pollen parent, "Pinocchio," my new variety is also definitely distinct therefrom, as evidenced by the fact that the blooms of the new variety are multicolored (basically yellow, with some markings of pink and salmon), whereas the blooms of "Pinocchio" are best described as pink suffused salmon; the foliage of my new variety is medium to large in size and in abundance thereof covers the plant well, whereas the foliage of "Pinocchio" is substantially smaller in size and less abundant; the blooms of my new variety are larger in size than those of this parent, being from 2½ inches to 3¼ inches in diameter, whereas the blooms of "Pinocchio" are usually small, i. e., about 2 inches in diameter and rarely more than 2½ inches; and the foliage of my new variety is semi-glossy, whereas that of "Pinocchio" is non-glossy.

Asexual reproduction of my new variety by budding, as performed at Ontario, California, shows that the foregoing characteristics and distinctions of my new variety come true to form and are established and transmitted through succeeding propagations.

The accompanying drawing shows typical specimens of the blooms and foliage of my new variety in different stages of development, as depicted in color as nearly true as it is reasonably possible to make the same color illustration of this character.

The following is a detailed description of my new variety, with color terminology in accordance with Robert F. Wilson's Horticultural Colour Chart (hereinafter abbreviated as "Wilson") and Ridgway's Color Standards and Nomenclature (hereinafter abbreviated as "Ridgway"):

Type: Bush; outdoor; seedling; for garden decoration.
Class: Hybrid polyantha.
Breeding: Seedling.
*Seed parent.*—"Fandango."
*Pollen parent.*—"Pinocchio."
Propagation: Holds its distinguishing characteristics through succeeding propagations by budding.

FLOWER

Locality where grown and observed: Ontario, California.
Flowers borne: Usually several to stem; in irregular to regular rounded clusters; on strong, medium length stems.
Quantity of bloom: Free to abundant, outdoors.
Continuity: Continuous during growing season.
Fragrance: Moderate. Nature—tea to spicy.
Bud:
*Peduncle.*—Average length, but sometimes long; average caliper; erect; moderately smooth; numerous gland-tipped cilia; few soft prickles. Color—between Lettuce Green, Plate V (Ridgway) and Parrot Green, Plate VI (Ridgway), overlaid with near Indian Red, Plate XXVII (Ridgway) on side exposed to the sun.
*Before calyx breaks.*—Size—medium. Form—medium length; ovoid; with foliaceous appendages; some tomentum; with few gland-tipped cilia on the surface of the bud; usually without much-cut foliaceous parts extending beyond the tip of the bud.
*As calyx breaks.*—Color—near Primrose Yellow, Plate 601/2, page 65 (Wilson), very heavily overlaid with between Currant Red, Plate 821/1, page 167 (Wilson) and Cardinal Red, Plate 822/1, page 168 (Wilson).
*Sepals.*—Inner surface with fine woolly tomentum; margins of alternate sepals lined with fine woolly tomentum; others lined with gland-tipped cilia.
*As first petal opens.*—Size—average to large for class. Form—medium length; urn-shaped. Color: Outside—between Saffron Yellow, Plate 7/3, page 7 (Wilson) and Cadmium Orange, Plate 8/3, page 8 (Wilson), overlaid somewhat with between Mandarin Red, Plate 17/2, page 17 (Wilson) and Vermillion, Plate 18/2, page 18 (Wilson); sometimes also marked with between Geranium Lake, Plate 20/2, page 20 (Wilson) and Carmine, Plate 21/1, page 21 (Wilson); area at base of petal near attachment equal to approximately ⅙ size of the petal between Aureolin, Plate 3/2, page 3 (Wilson) and Aureolin, Plate 3/1, page 3 (Wilson). Inside—between Saffron Yellow, Plate 7/3, page 7 (Wilson) and Cadmium Orange, Plate 8/3, page 8 (Wilson), overlaid somewhat with between Poppy Red, Plate 16/3, page 16 (Wilson) and Mandarin Red, Plate 17/3, page 17 (Wilson); area at base of petal near attachment equal to approximately ⅙ size of the petal between Aureolin, Plate 3/2, page 3 (Wilson) and Aureolin, Plate 3/1, page 3 (Wilson).
*Opening.*—Opens up well; is not retarded from opening by cold, hot, wet or dry weather.
Bloom:
*Size (when fully open).*—Average; from 2½ inches to 3¼ inches.
*Petalage.*—Very double; from 45 to 58 petals, plus 8 to 15 petaloids; arranged regularly.
*Form.*—High-centered at first; becoming flat to open later; petals being at first somewhat cupped, with lateral margins reflexed for approximately ¼ to ⅓ of petal length; lateral margins of outer petals sometimes reflexed ½ to ¾ of petal length; apex reflexed only slightly except on some of the outer petals where occasionally they are reflexed from ⅓ to ½ of their petal length; petals becoming later at maturity flat-cupped, with lateral margins usually reflexed about ½ of petal length; lateral margins of some of the outer petals sometimes reflexed ¾ or more of petal length, and apex of some petals reflexed ⅓ to ½ of petal length.

Petals:

*Texture.*—Thick; leathery; with both inside and outside slightly shiny to satiny.

*Shape.*—Outside—broadly obovate, with apex flat; rarely with 1 notch. Intermediate—obovate, with apex rounded to flat; rarely with 1 notch. Inside—narrowly obovate, with apex rounded; sometimes with 1 or 2 notches.

This description of a newly opened flower was made from a rose grown outdoors in the month of October, at Ontario, California:

Color:

*Outside petal.*—Outside surface—between Buttercup Yellow, Plate 5/3, page 5 (Wilson) and Indian Yellow, Plate 6/3, page 6 (Wilson), overlaid somewhat with between Carmine, Plate 21/2, page 21 (Wilson) and Crimson, Plate 22/2, page 22 (Wilson); small area at base of petal near attachment between Aureolin, Plate 3/2, page 3 (Wilson) and Aureolin, Plate 3/1, page 3 (Wilson). Inside surface—between Indian Yellow, Plate 6/3, page 6 (Wilson) and Saffron Yellow, Plate 7/3, page 7 (Wilson), overlaid slightly with near Scarlet, Plate 19/3, page 19 (Wilson) particularly around upper margin of the petal; area at base of petal near attachment near Aureolin, Plate 3/1, page 3 (Wilson).

*Intermediate petal.*—Outside surface—between Indian Yellow, Plate 6/3, page 6 (Wilson) and Saffron Yellow, Plate 7/3, page 7 (Wilson), only slightly overlaid with near Scarlet, Plate 19/3, page 19 (Wilson); small area at base of petal near attachment near Aureolin, Plate 3/1, page 3 (Wilson). Inside surface—between Indian Yellow, Plate 6/3, page 6 (Wilson) and Saffron Yellow, Plate 7/3, page 7 (Wilson), only very slightly overlaid with near Scarlet, Plate 19/3, page 19 (Wilson); area at base of petal near attachment near Aureolin, Plate 3/1, page 3 (Wilson).

*Inner petal.*—Outside surface—between Indian Yellow, Plate 6/3, page 6 (Wilson) and Saffron Yellow, Plate 7/3, page 7 (Wilson), only slightly overlaid with near Scarlet, Plate 19/3, page 19 (Wilson); small area at base of petal near attachment near Aureolin, Plate 3/1, page 3 (Wilson). Inside surface—between Indian Yellow, Plate 6/3, page 6 (Wilson) and Saffron Yellow, Plate 7/3, page 7 (Wilson), only very slightly overlaid with near Scarlet, Plate 19/3, page 19 (Wilson); area at base of petal near attachment near Aureolin, Plate 3/1, page 3 (Wilson).

This description was made from a rose that was open for 3 days outdoors in the month of November, at Ontario, California:

Color:

*Outside petal.*—Outside surface—between Aureolin, Plate 3/3, page 3 (Wilson) and Lemon Yellow, Plate 4/3, page 4 (Wilson), heavily overlaid with between Carmine, Plate 21/2, page 21 (Wilson) and Carmine, Plate 21/1, page 21 (Wilson) on upper ½ of petal; area at base of petal near attachment near Aureolin, Plate 3/2, page 3 (Wilson). Inside surface—between Aureolin, Plate 3/2, page 3 (Wilson) and Lemon Yellow, Plate 4/3, page 4 (Wilson), heavily overlaid with between Geranium Lake, Plate 20/2, page 20 (Wilson) and Geranium Lake, Plate 20/1, page 20 (Wilson); area at base of petal near attachment near Aureolin, Plate 3/2, page 3 (Wilson).

*Inside petal.*—Outside surface—between Aureolin, Plate 3/2, page 3 (Wilson) and Lemon Yellow, Plate 4/3, page 4 (Wilson), overlaid somewhat, particularly on upper portion of petal near margins with near Geranium Lake, Plate 20/2, page 20 (Wilson); area at base of petal near attachment near Aureolin, Plate 3/2, page 3 (Wilson). Inside surface—between Aureolin, Plate 3/2, page 3 (Wilson) and Lemon Yellow, Plate 4/3, page 4 (Wilson), heavily overlaid with between Geranium Lake, Plate 20/2, page 20 (Wilson) and Geranium Lake, Plate 20/1, page 20 (Wilson); area at base of petal near attachment near Aureolin, Plate 3/2, page 3 (Wilson).

General color effect:

*Newly opened flower.*—Between Saffron Yellow, Plate 7/3, page 7 (Wilson) and Saffron Yellow, Plate 7/2, page 7 (Wilson), with markings of between Vermillion, Plate 18/3, page 18 (Wilson) and Scarlet, Plate 19/3, page 19 (Wilson); area at base of petal near attachment near Aureolin, Plate 3/1, page 3 (Wilson).

*3-days open.*—Between Aureolin, Plate 3/2, page 3 (Wilson) and Lemon Yellow, Plate 4/3, page 4 (Wilson), heavily overlaid particularly on upper portion of petal with between Geranium Lake, Plate 20/2, page 20 (Wilson) and Geranium Lake, Plate 20/1, page 20 (Wilson); area at base of petal near attachment near Aureolin, Plate 3/2, page 3 (Wilson).

Behavior: Drop off cleanly; not particularly affected by cold, hot, wet or dry weather.

Flower longevity: On bush in garden—4 days in November. Cut roses grown outdoors and kept at living-room temperatures—4 or 5 days in November.

REPRODUCTIVE ORGANS

Stamens: Average number to many; arranged regularly about pistils; a few mixed with petaloids.

Filaments: Medium length: from 6 to 10 mm. in length; most with anthers.

*Color.*—Near Lemon Yellow, Plate 4, page 4 (Wilson).

Anthers: Medium size; all open approximately at once.

*Color.*—Upper side—margins near Buttercup Yellow, Plate 5/1, page 5 (Wilson); remainder near Canary Yellow, Plate 2/3, page 2 (Wilson). Under side—margins near Buttercup Yellow, Plate 5/1, page 5 (Wilson); remainder near Canary Yellow, Plate 2/3, page 2 (Wilson).

Pollen: Moderate to abundant.

*Color.*—Near Indian Yellow, Plate 6/2, page 6 (Wilson).

Pistils: Average number; approximately 75 in number.

Styles: Moderately even; average length; thin to average caliper; bunched; from 5 to 9 mm. in length.

*Color.*—Upper ⅓ to ½ of style near Carmine, Plate 21/1, page 21 (Wilson); remainder near Primrose Yellow, Plate 601/3, page 65 (Wilson).

Stigma: Color—near Empire Yellow, Plate 603/1, page 66 (Wilson).

Ovaries: Most enclosed in, but few protruding from calyx.

Hips: Average length; globular; smooth; walls thick and and fleshy.

*Color (mature).*—Between Saffron Yellow, Plate 7/1, page 7 (Wilson) and Cadmium Orange, Plate 8/1, page 8 (Wilson).

Sepals: Permanent; medium length; recurved.

*Color.*—Inside—near Biscay Green, Plate XVII (Ridgway), overlaid somewhat with near Indian Red, Plate XXVII (Ridgway) and masked by White wooly tomentum. Outside—between Courge Green, Plate XVII (Ridgway) and Biscay Green, Plate XVII (Ridgway); sometimes overlaid somewhat with near Mineral Red, Plate XXVII (Ridgway).

Seeds: Average number to many; medium size; from 12 to 25 in number.

PLANT

Foliage:

*Leaves.*—Compound of usually 5 to 7 leaflets; abundant; medium to large in size; leathery; semi-glossy.

*Leaflets.*—Shape—ovoid, with apex acute. Base—round. Margin—simply serrate.

*Color.*—Mature: Upper surface—near Dark Dull Yellow—Green, Plate XXXII (Ridgway); under surface—near Chromium Green, Plate XXXII (Ridgway). Young: Upper surface—between Yew Green, Plate XXXI (Ridgway) and Cress Green, Plate XXXI (Ridgway), heavily overlaid with near Dark Corinthian Purple, Plate XXXVIII (Ridgway); under surface—between Corinthian Purple, Plate XXXIII (Ridgway) and Neutral Red, Plate XXXVIII (Ridgway).

*Rachis (the supporting stem of the compound leaf).*—Average size. Upper side—grooved, hairy, and with many stipitate glands on edges. Under side—prickly, and with some stipitate glands.

*Stipules.*—Medium length to long; medium width; with medium length points turning out at an angle of more than 45°.

*Disease resistance.*—Average resistance to mildew as compared with other varieties grown under comparable cultural conditions at Ontario, Calif.

Growth:

*Habit.*—Bushy; much-branched.

*Growth.*—Free to vigorous.

*Canes.*—Medium caliper.

*Main stems.*—Color—between Oil Green, Plate V (Ridgway) and Spinach Green, Plate V (Ridgway). Large prickles—several to many; medium length; hooked slightly downward; with moderately long, narrow base. Color—between Fawn Color, Plate XL (Ridgway) and Army Brown, Plate XL (Ridgway). Small Prickles—few. Color—between Fawn Color, Plate XL (Ridgway) and Army Brown, Plate XL (Ridgway). Hairs—none.

*Branches.*—Color—between Biscay Green, Plate XVII (Ridgway) and light Elm Green, Plate XVII (Ridgway). Large prickles—several to many; medium length; hooked slightly downward; with moderately long, narrow base. Color—near Fawn Color, Plate XL (Ridgway). Small prickles—several. Color—near Fawn Color, Plate XL (Ridgway). Hairs—none.

*New shoots.*—Color—between Courge Green, Plate XVII (Ridgway) and Biscay Green, Plate XVII (Ridgway), heavily overlaid with near Dark Corinthian Purple, Plate XXXVIII (Ridgway). Large prickles—several; medium length; hooked slightly downward; with moderately long, narrow base. Color—near Vernonia Purple, Plate XXXVIII (Ridgway); point near Kildare Green, Plate XXXI (Ridgway). Small prickles—several. Color—near Vernonia Purple, Plate XXXVIII (Ridgway). Hairs—none.

I claim:

A new and distinct variety of rose plant of the hybrid polyantha class, substantially as herein shown and described, characterized particularly as to novelty by the combination of a distinctive color progression of its blooms from Yellow with some markings of pink and salmon, at first, to almost entirely pink and salmon in the older blooms, by the moderate fragrance and good petal substance of its blooms, with attendant long-lasting quality thereof, by the very double petalage and the many-flowered cluster habit of its blooms, and by its abundant and semi-glossy foliage.

No references cited.